United States Patent [19]

Tedder

[11] Patent Number: 4,772,849
[45] Date of Patent: Sep. 20, 1988

[54] ROTATING PROBE HEAD FOR TUBE INSPECTION

[75] Inventor: Joseph A. Tedder, Windsor, Conn.

[73] Assignee: Combustion Engineering, Inc., Windsor, Conn.

[21] Appl. No.: 906,048

[22] Filed: Sep. 11, 1986

[51] Int. Cl.$^4$ .............. G01N 27/90; G01N 29/06; F01B 3/00

[52] U.S. Cl. .............. 324/220; 33/178 E; 73/623; 74/89.15; 92/31

[58] Field of Search .............. 324/219–221, 324/226; 15/26; 81/DIG. 2; 74/89.15; 92/31–33; 73/623; 33/178 E, 178 F

[56] References Cited

U.S. PATENT DOCUMENTS

| | | | |
|---|---|---|---|
| 965,009 | 7/1910 | Philbrick | 92/31 X |
| 2,036,582 | 4/1936 | Kollsman | 92/31 X |
| 2,684,464 | 7/1954 | Hastings et al. | 324/220 |
| 3,551,931 | 1/1971 | Monroe et al. | 74/89.15 X |
| 3,831,084 | 8/1974 | Scalese et al. | 324/219 X |
| 4,438,399 | 3/1984 | Schnabl et al. | 324/220 |
| 4,441,078 | 4/1984 | Lecomte | 324/219 |
| 4,625,165 | 11/1986 | Rothstein | 324/220 |

Primary Examiner—Gerard R. Strecker
Attorney, Agent, or Firm—John H. Mulholland

[57] ABSTRACT

A probe (10) for longitudinally traversing and circumferentially inspecting the interior of a tube. A rotating sensor containing head (44) is driven by a rotor (40) extending from the end (38) of a cylindrical housing (12) in which it is mounted. The axially fixed rotor (40) surrounds and is driven by a helix drive connection (70) to a piston extension (32). The piston (20) reciprocates in a cylindrical chamber (14) within the housing (12) in response to selectively applied fluid pressure acting against a spring bias (60). A strain gage (62) on the spring (60) controls the fluid pressure by means of valve (2) whereby reciprocation of the piston (20) and its extension (32) rotates the rotor (40) by means of the helical groove (70) and balls (72). The various parts are hollow to accommodate the necessary wire conductors (51 and 64) and H$_2$O.

12 Claims, 1 Drawing Sheet

ROTATING PROBE HEAD FOR TUBE INSPECTION

FIELD OF THE INVENTION

The present invention relates to an apparatus for inspecting the walls of a cylindrical conduit or tube, and more particularly, an apparatus for inspecting a tube utilizing the induction of an eddy current or sound wave energy within said wall to provide an indication of wall integrity.

BACKGROUND OF THE INVENTION

Inspection of tubes or other conduits for defects or wear within the walls is a necessary and time-consuming task for owners and operators of processes and equipment wherein high pressure fluid is transferred. Although many techniques have been developed and used in the prior art for inspecting newly manufactured tubing, it is the inspection of installed tubing which presents the greatest challenge to those in the industry. This is due to two factors: the difficulty in accessing sections of the installed tubing which may be within a tube bank or pressure vessel, as well as the possibility that significant structural degradation is likely to have occurred after an extended period of operation under conditions of high pressure, high temperature, and/or corrosive environment.

One such application wherein inspection of the structural integrity of an installed tube is critical is in the steam generators of a nuclear powered electric generating plant. In such a plant, the heated primary coolant flows through a plurality of inverted U-shaped tubes immersed in water from which steam is generated.

As it is typical in such an application for the primary side coolant pressure to be higher than that of the secondary, steam producing side, it is apparent that a failure of a steam generator tube will cause a leakage from the primary coolant into the secondary system.

The occurrence of such leakage is not unusual in such units, especially after extended periods of operation. For this reason, inspection of the individual steam generator U tubes is performed at regular intervals while the plant is shut down for service. An effective test program will not only locate specific failures that have already occurred in the steam generator tubing, but also attempt to identify the specific locations where a failure may be likely to soon occur. Thus, a high accuracy and sensitivity in the testing apparatus is a very desirable feature and has been the goal of the test apparatus heretofore in use and well known in the prior art.

One method of sensing anomalies in a metal structure utilizes the electrical eddy currents set up when a magnetic field and a conductive metal structure are moved relative to each other. The electrical eddy currents induced by such movements may be monitored by a magnetic field sensor and the results analyzed to determine the condition of the inspected metal structure. Eddy current probes are shown in U.S. Pat. No. 4,438,399 to Schnabl et al and U.S. patent application Ser. No. 693,427, filed Jan. 22, 1985 and assigned to the same assignee as the instant invention.

Another method of sensing anomalies in a metal structure utilizes ultrasonic wave patterns set up in the structure by one transducer and sensed by another.

In either inspection method, it would be useful to have a probe of simple and reliable design for both circumferentially and longitudinally traversing the interior of a nuclear steam generator tube, or the like, to be inspected. A simple, low cost rotating head for mounting the inspection sensors, whether they be eddy current coils or ultrasonic transducers, accordingly is provided. With the sleeving of failed tubes currently presenting an economically and technically beneficial alternative to the former practice of simply plugging off the failed tube in a nuclear steam generator, the need for such an inspection apparatus is readily apparent to those skilled in the art.

SUMMARY OF THE INVENTION

The present invention provides a probe for examining the interior of a tube wherein the probe includes means for rotating eddy current and ultrasonic sensors for determining material imperfections circumferentially. The outstanding features of the novel mechanism include its low cost, its simplicity, its reliability and its small size. In its simplest form, the unit will turn the rotating head past 360° to approximately 450°. However, a greater rotation is possible with minor changes to accommodate the conductors. In use, the assembly is attached to a plastic tube and driven into the steam generator tubes to the desired test position by a device known as a probe pusher.

The rotating sensor containing head is driven by a rotor extending from the end of a cylindrical housing in which it is mounted. The axially fixed rotor surrounds and is driven by a helix drive connection to a piston extension. The piston recriprocates in a cylindrical chamber within the housing in response to selectively applied fluid pressure acting against a spring bias. A strain gage on the spring may control the pressure whereby reciprocation of the piston and its extension rotates the rotor by means of the helix drive. In the alternative, water may be applied in the form of a pressure ramp, compressing the spring accordingly. The various parts are hollow to accommodate the necessary wire conductors between the sensors in the rotating head and chart recorders and tape recorders or other signal display devices.

In operation, pressured water is applied to the piston in the cylinder to force it longitudinally against the bias of the spring. A slot and pin arrangement is provided which allows a helix driving means on the piston extension to move longitudinally only. Balls in the groove of the helix and a groove in the rotor convert the longitudinal motion of the helix groove to rotational motion of the rotor. Upon reducing the water pressure to zero or its original pressure, the spring returns the piston and reverses the rotation of the rotor head to its original circumferencial position. The entire probe may be moved longitudinally and the process then repeated.

The precise circumferential position is provided by means of the strain gage on the spring as well as the water pressure control and consequent rotational motion and position.

The present invention, therefore, provides a probe which is able to provide complete inspection coverage by sensors for the full circumference and length of the tube.

DESCRIPTION OF THE PREFERRED EMBODIMENT

Figure 1:
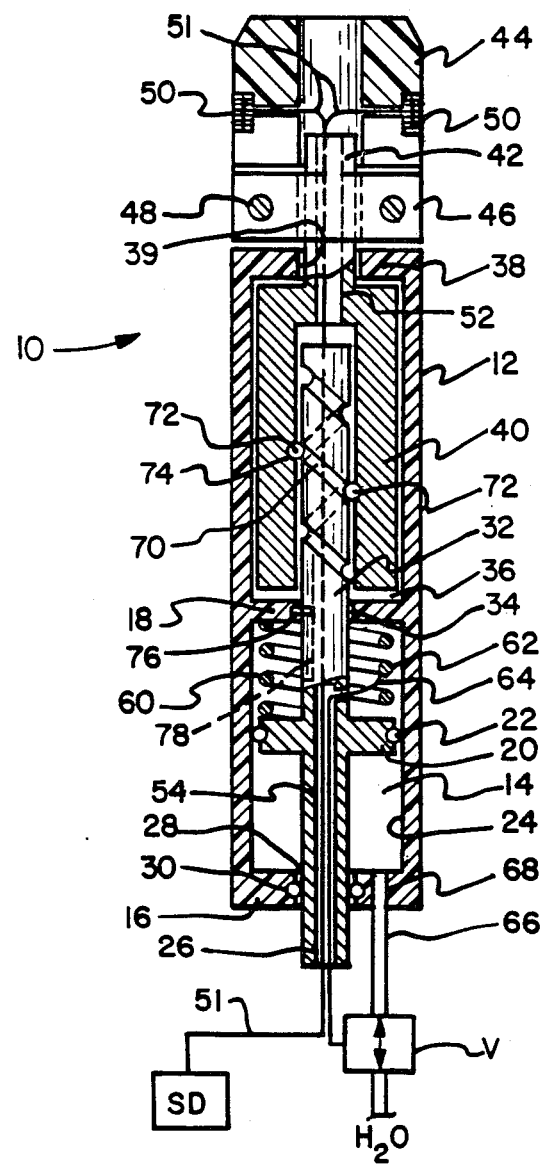
FIG. 1 is a schematic sectional view, with parts broken away for clarity, of the probe of the invention for longitudinally traversing and circumferentially inspecting the interior of a tube.

The probe for longitudinally traversing and circumferentially inspecting the interior of a tube is generally designated by the numeral 10 in the drawing. The probe 10 includes a substantially hollow housing 12 of a high temperature plastic material called Torlon which is a polyamideimide material manufactured by AMOCO. The Torlon housing 12 includes a cylinder chamber 14 defined by end walls 16 and 18. The end wall 16 is also an end wall of the housing 12. A hollow piston 20 in the form of a machined stainless steel elongated body is reciprocally mounted in the cylindrical chamber 14. An O-ring 22 of Buna-N material creates a sliding fluid seal between piston 20 and the wall 24 of the cylinder chamber 14.

The stainless steel piston 20 includes a first axial piston extension 26 concentric with cylinder chamber 14. The piston extension 26 projects through and beyond and reciprocates in the concentric opening 28 in end wall 16. An O-ring 30 provides a sliding fluid seal between the piston extension 26 and the opening 28 in end wall 16. A second axial extension 32 on the piston 20 projects opposite the first axial piston extension 26 through an opening 34 in cylinder chamber end wall 18. Piston extension 32 extends into a second chamber 36 within the housing 12 on the side of the end wall 18 opposite cylinderical chamber 14. The second chamber 36 has an end wall 38 which is also an end wall of housing 12. A concentric opening 39 is provided in end wall 38. A hollow rotor 40 is axially confined within chamber 36 and radially surrounds the second piston extension 32. The rotor 40 has a concentric extension 42 projecting through opening 39 and beyond end wall 38. The rotor 40 and its extension 42 are preferably made of a material such as stainless steel.

Mounted on the end of extension 42 beyond end wall 38 of housing 12 is a rotating head 44 made of LEXAN which is a polycarbonate material made by General Electric Corporation or can be made from other materials such as PLEXIGLAS, on acrylic mataerial from Rohm and Haas. The rotating head 44 is suitably secured to rotor extension 42 as by clamp means 46 and fasteners 48. Sensors in the form of eddy current coils 50 are mounted in the rotating head for circumferential inspection of a tube. Conductive wires 51 from the coils 50 extend through a central opening 52 in rotor 40 and its extension 42 and through a central opening 54 in piston 20 and its extensions 32 and 26 to an external signal display, chart recorder or tape recorder apparatus schematically indicated SD in the drawing.

A spring means 60 urges piston 20 in a direction away from the direction in which the axial piston extension 32 projects. A strain gage connected at 62 to spring 60 transmits a signal via conductive wires 64 to a solenoid valve V or other suitable pressurized flow controlling device. This ensures that fluid pressure applied through a conduit 66, such as a feedwater from a pressurized source (not shown), may pass through end wall 16 by means of opening 68 and into the cylinder chamber 14 where it acts on piston 20 against the urging of spring 60. The strain gage 62, thus, may provide precise circumferential position to the rotor 44 because the axial position of the piston 20 is controlled by the fluid pressure in chamber 14. This permits the piston extension 32 to accurately drive rotor 40 and thus rotating head 44 through a helical drive means 70. The helical drive means 70 includes a helical groove in the piston 32 which, by means of balls 72 and groove 74 in axially fixed rotor 40, is equivalent to a lead-screw/nut mechanism.

When pressurized water is supplied through solenoid valve V to the cylinder 14, the piston 20 is forced longitudinally, compressing the spring 60. A pin 76, with an end riding in a slot 78 in piston extension 32, allows the piston to move longitudinal only and prevents its rotational movement. Thus, the helix ball arrangement 70 converts the longitudinal motion of the helix portion of piston extension 32 into rotational motion of the rotor 40.

Because of the limited length of the wires 51, and the limited travel of the piston 20, the probe has limited rotational freedom, typically 450°. It is important, however, only that the sensors in the head 44 may be rotated 360° for inspection of the tube. It should be clear from the description above that the coils 50 could be transducers for purposes of ultrasonic testing and the probe of the invention would operate in the same manner.

It will be appreciated by those skilled in the art that the probe, according to the preferred embodiment of the present invention, is able to conduct a complete examination of the entire tube wall in a single longitudinal pass through the subject tube.

The completeness and accuracy of the tube inspection provided by the probe according to the present invention can greatly reduce the time spent in inspecting and therefore servicing the steam generators of nuclear electric power generating stations. Reduced maintenance time translates into reduced time offline and increased plant productivity.

It is to be understood that the appended drawing figure and proceeding discussion have been directed primarily toward the illustrative, preferred embodiment of the present invention, and that equivalent embodiments utilizing functionally and/or structurally equivalent components which are or become apparent to those skilled in the art are also within the scope of the proceeding disclosure and the following claims.

I claim:

1. A probe for longitudinally traversing the interior of an elongated tube comprising:
    a substantially hollow housing;
    a cylinder chamber within said housing defined by two end walls;
    a hollow piston reciprocally mounted in said cylinder chamber;
    a fluid seal between said cylinder chamber wall and said piston;
    said piston including a first axial piston extension concentric with said cylinder chamber projecting and reciprocating in a concentric opening in a first one of said cylinder chamber end walls;
    said piston further including a second axial piston extension opposite said first axial piston extension concentric with said cylinder chamber projecting through and beyond and reciprocating in an opening through a second one of said cylinder chamber end walls;
    a second chamber within said housing on the side of said second end wall opposite said cylinder chamber into which said second piston extension projects;
    said second chamber having an end wall opposite said second end wall which defines a housing end wall with a concentric opening;

a hollow rotor axially fixed and rotationally mounted to radially surround said second piston extension;

a concentric rotor extension projecting through and beyond the concentric opening of said housing end;

a rotational head mounted on said rotor extension;

means for urging said piston in a direction away from the direction in which said second axial piston extension projects;

means for selectively controlling fluid pressure in said cylinder chamber acting to move said piston against said urging; and, means for preventing rotation and for allowing reciprocation of said piston;

means for providing a helical drive connection between said second axial piston extension and said rotor such that reciprocation of said piston rotates said rotor.

2. The probe of claim 1 in which the first axial piston extension extends beyond and projects through the opening in said first one of said cylinder chamber end walls and means provide a sliding seal engagement therewith.

3. The probe of claim 2 in which the means urging the piston in a direction away from the direction in which said second axial piston extension projects is a spring within said cylinder chamber between the piston and the second one of said cylinder chamber end walls.

4. The probe of claim 3 in which a strain gage is connected to sense strain in the spring and wires from the strain gage extend into the hollow piston and its extension beyond the first one of said cylinder chamber end walls for connection to said means selectively controlling fluid pressure in said cylinder chamber, whereby fluid pressure applied is in proportion to the extent of piston travel against the spring urging, as sensed from the spring.

5. The probe of claim 1 in which the means selectively controlling fluid pressure is a solenoid valve in a line from a pressurized fluid source.

6. The probe of claim 1 in which the means preventing rotation and allowing reciprocation of said piston is a fixed pin and a longitudinal slot in said piston containing an end of said fixed pin.

7. The probe of claim 1 in which the rotational head includes a sensor for 360° inspection of the tube.

8. The probe of claim 7 in which wires from the sensor extend longitudinally from the rotational head through the hollow rotor and hollow piston and their respective extensions.

9. The probe of claim 7 in which the sensor is either an eddy current sensor or an ultrasonic transducer.

10. The probe of claim 1 in which the fluid is water.

11. The probe of claim 1 in which the helical drive means includes rotating balls containing grooves in the rotor and the second axial piston extension.

12. A probe for longitudinally traversing the interior of an elongated tube comprising:

a substantially hollow elongated housing;

a cylinder chamber within said housing defined by two end walls;

a hollow piston reciprocally mounted in said cylinder chamber;

a fluid seal between said cylinder chamber wall and said piston;

said piston including an axial piston extension concentric with said cylinder chamber projecting through and beyond and reciprocating in an opening through one of said cylinder chamber end walls;

a second chamber within said housing on the side of said one end wall opposite said cylinder chamber into which said piston extension projects;

a hollow rotor axially fixed and rotationally mounted to radially surround said piston extension;

a concentric rotor extension projecting beyond the end of said housing;

a rotational head mounted on said rotor extension;

means for urging said piston in a direction away from the direction of said rotational head;

means for selectively controlling fluid pressure in said cylinder chamber acting to move said piston against said urging;

means for preventing rotation and for allowing reciprocation of said piston; and, means for converting the reciprocal motion of said piston to rotary motion of the rotor.

* * * * *